(12) United States Patent
Salnik et al.

(10) Patent No.: US 7,499,168 B2
(45) Date of Patent: Mar. 3, 2009

(54) COMBINED MODULATED OPTICAL REFLECTANCE AND ELECTRICAL SYSTEM FOR ULTRA-SHALLOW JUNCTIONS APPLICATIONS

(75) Inventors: Alex Salnik, Castro Valley, CA (US); Lena Nicolaides, Castro Valley, CA (US); Jon Opsal, Livermore, CA (US)

(73) Assignee: KLA-Tencor Corp., Milpitas, CA (US)

( * ) Notice: Subject to any disclaimer, the term of this patent is extended or adjusted under 35 U.S.C. 154(b) by 83 days.

(21) Appl. No.: 11/656,610

(22) Filed: Jan. 23, 2007

(65) Prior Publication Data

US 2007/0188761 A1 Aug. 16, 2007

Related U.S. Application Data

(60) Provisional application No. 60/772,892, filed on Feb. 14, 2006.

(51) Int. Cl.
*G01N 21/00* (2006.01)

(52) U.S. Cl. ....................... 356/432; 356/445

(58) Field of Classification Search ......... 356/432–440, 356/445–448, 237.1–237.5; 374/5
See application file for complete search history.

(56) References Cited

U.S. PATENT DOCUMENTS

| | | | |
|---|---|---|---|
| 4,521,118 A | 6/1985 | Rosencwaig | 374/5 |
| 4,522,510 A | 6/1985 | Rosencwaig et al. | 374/7 |
| 4,634,290 A | 1/1987 | Rosencwaig et al. | 374/5 |
| 4,636,088 A * | 1/1987 | Rosencwaig et al. | 374/5 |
| 4,646,088 A | 2/1987 | Inoue | 340/870.31 |
| 4,679,946 A | 7/1987 | Rosencwaig et al. | 374/5 |
| 4,795,260 A * | 1/1989 | Schuur et al. | 356/400 |
| 4,854,710 A | 8/1989 | Opsal et al. | 356/432 |
| 5,074,669 A * | 12/1991 | Opsal | 356/445 |
| 5,074,699 A | 12/1991 | Blaisdell et al. | 403/122 |
| 5,159,410 A * | 10/1992 | Pollak et al. | 356/417 |
| 5,228,776 A * | 7/1993 | Smith et al. | 374/5 |
| 5,706,094 A * | 1/1998 | Maris | 356/432 |
| 5,854,719 A | 12/1998 | Ginosar et al. | 360/69 |
| 5,978,074 A | 11/1999 | Opsal et al. | 356/72 |
| 6,075,603 A * | 6/2000 | O'Meara et al. | 356/496 |
| 6,268,916 B1 | 7/2001 | Lee et al. | 356/369 |
| 6,271,921 B1 * | 8/2001 | Maris et al. | 356/432 |

(Continued)

OTHER PUBLICATIONS

2005 Brochure from Frontier Semiconductor, San Jose, California, entitled "FSM RsL 100 Sheet Resistance and Leakage Current Mapping Tool Non-contact Sheet Resistance and Leakage Current Measurements for Implant & Annealing Monitoring for 65 and 45 nm CMOS Technologies," 1 page in length.

(Continued)

*Primary Examiner*—Hoa Q Pham
(74) *Attorney, Agent, or Firm*—Stallman & Pollock LLP

(57) ABSTRACT

A metrology tool for semiconductor wafers is disclosed which combines modulated reflectivity measurement with junction photovoltage measurements. The tool includes an intensity modulated pump beam for periodically exciting the sample. A separate probe beam is used to monitor changes in optical reflectivity of the sample. In addition, capacitive electrodes are provided to measure modulated changes in the voltage across the electrodes. These measurements are combined to evaluate the wafer. These measurement can be particularly useful in characterizing ultrashallow junctions.

10 Claims, 1 Drawing Sheet

U.S. PATENT DOCUMENTS

| | | | |
|---|---|---|---|
| 6,452,685 B2 | 9/2002 | Opsal et al. | 356/601 |
| 6,989,899 B2 | 1/2006 | Salnik et al. | 356/432 |
| 7,362,441 B2 * | 4/2008 | Opsal et al. | 356/445 |
| 2004/0251927 A1 | 12/2004 | Salnik et al. | 324/765 |
| 2005/0195399 A1 | 9/2005 | Nicolaides et al. | 356/432 |
| 2006/0166385 A1 | 7/2006 | Salnik et al. | 438/17 |

OTHER PUBLICATIONS

V.N. Faifer et al., "Non-Contact Sheet Resistance and Leakage Current Mapping for Ultra-Shallow Junctions," *Journal of Vacuum Science & Technology B: Microelectronics and Nanometer Structures,* vol. 24, Issue 1, Jan. 2006, pp. 414-420.

V.N. Faifer et al., "Non-contact Electrical Measurements of Sheet Resistance and Leakage Current Density for Ultra-shallow (and other) Junctions," *Mat. Res. Soc. Symp. Proc.,* vol. 810 (2004) pp. 475-480.

L. Nicolaides et al., "Nondestructive analysis of ultrashallow junctions using thermal wave technology," *Review of Scientific Instruments,* vol. 74, No. 1, Jan. 2003, pp. 586-588.

A. Salnick et al., "Simultaneous determination of ultra-shallow junction depth and abruptness using thermal wave technique," *Review of Scientific Instruments,* vol. 75, No. 6, Jun. 2004, pp. 2144-2148.

* cited by examiner

COMBINED MODULATED OPTICAL REFLECTANCE AND ELECTRICAL SYSTEM FOR ULTRA-SHALLOW JUNCTIONS APPLICATIONS

PRIORITY

This application claims priority to U.S. Provisional Application Ser. No. 60/772,892, filed Feb. 14, 2006, and incorporated herein by reference.

TECHNICAL FIELD

The subject invention relates to a combination of optical and electrical devices used to non-destructively evaluate semiconductor wafers. In particular, the present invention relates to systems for measuring multiple parameters of ultra-shallow junctions formed in semiconductor samples.

BACKGROUND OF THE INVENTION

As geometries continue to shrink, manufacturers have increasingly turned to optical techniques to perform non-destructive inspection and analysis of semiconductor wafers. The basis for these techniques is the notion that a sample may be examined by analyzing the reflected energy that results when an optical beam is directed at a sample. This type of inspection and analysis is known as optical metrology and is performed using a range of different optical techniques.

One widely used type of optical metrology system includes a pump laser. The pump laser is switched on and off to create an intensity-modulated pump beam. The pump beam is projected against the surface of a sample causing localized heating of the sample. As the pump laser is modulated, the localized heating (and subsequent cooling) creates a train of thermal and plasma waves within the sample. These waves reflect and scatter off various features and interact with various regions within the sample in a way that alters the flow of heat and/or plasma from the pump beam spot.

The presence of the thermal and plasma waves has a direct effect on the surface reflectivity of the sample. Features and regions below the sample surface that alter the passage of the thermal and plasma waves will therefore alter the optical reflective patterns at the surface of the sample. By monitoring the changes in reflectivity of the sample at the surface, information about characteristics below the surface can be investigated.

To monitor the surface changes, a probe beam is directed at a portion of the sample that is illuminated by the pump laser. A photodetector records the intensity of the reflected probe beam. The output signal from the photodetector is filtered to isolate the changes that are synchronous with the pump beam modulation. For most implementations, this is performed using a heterodyne or lock-in detector (See U.S. Pat. No. 5,978,074 and in particular FIG. 2 for a discussion of such a lock-in amplifier/detector). Devices of this type typically generate separate "in-phase" (I) and "quadrature" (Q) outputs. These outputs are then used to calculate amplitude and phase of the modulated signal using the following equations:

$$\text{Amplitude} = \sqrt{I^2 + Q^2} \quad (1)$$

$$\text{Phase} = \arctan(Q/I) \quad (2)$$

The amplitude and phase values are used to deduce physical characteristics of the sample. In most cases, this is done by measuring amplitude values (amplitude is used more commonly than phase) for one or more specially prepared calibration samples, each of which has known physical characteristics. The empirically derived values are used to associate known physical characteristics with corresponding amplitude values. Amplitude values obtained for test samples can then be analyzed by comparison to the amplitude values obtained for the calibration samples.

Systems of this type (i.e., those using external means to induce thermal or plasma waves in the sample under study) are generally referred to as Modulated Optical Reflectance (MOR) type systems. MOR-type systems are used to study a range of attributes, including material composition and layer thickness. MOR-type systems and their associated uses are described in more detail in U.S. Pat. Nos. 4,634,290, 4,646,088, 4,679,946; 4,854,710, 5,854,719, 5,978,074, 5,074,699 and 6,452,685. Each of these patents is incorporated herein by reference.

Another important use of MOR-type systems is measurement and analysis of the dopants added to semiconductor wafers before and after their activation. Dopants are ions that are implanted to semiconductors during a process known as ion implantation. The duration and intensity of the ion implantation process (i.e., total exposure of the semiconductor wafer) controls the resulting dopant concentration. The ion energy used during the implantation process controls the depth of implant. Both concentration and depth are critical factors that determine the overall effectiveness of the ion implantation process.

MOR-type systems are typically used to inspect wafers at the completion of the ion implantation process. The ion implantation damages the crystal lattice as incoming ions come to rest. This damage is typically proportional to the concentration and depth of ions within the crystal lattice. This makes measurement of damage an effective surrogate for direct measurement of dopant concentration and depth.

For this purpose, a MOR-type optical metrology tool with advanced signal processing algorithm is used to record both quadrature (Q) and in-phase (I) components of the signal for a series of specially prepared calibration samples. The measurement method then performs a linear fit using the recorded points to define a calibration line within an I-Q plane. The slope of this line is defined by the implantation energy and the points along the line correspond to different dopant concentrations. Thus, the damage profile can be characterized by comparison of measured and calibration data in I-Q space. Characterization of samples using I and Q outputs is described in U.S. Pat. No. 6,989,899, assigned to the same assignee and incorporated here by reference.

Dopant activation after the ion implantation step is usually performed by rapidly heating and cooling the sample in a special chamber. This process is also known as annealing of semiconductor wafers. During the anneal process, dopant ions diffuse away from the surface and form a concentration profile within the sample. The transition between the implanted region containing activated dopants and the non-implanted substrate is commonly referred to as a junction. For advanced semiconductor manufacturing, it is generally desirable for the implanted and activated region to be shallow, typically 500 Å or less. Devices of this type are generally referred to as having ultra-shallow junctions or USJ.

A number of techniques have been developed to characterize the effectiveness of USJ process. Destructive and contact methods include secondary ion mass spectroscopy (SIMS), transmission electron microscopy (TEM), and spreading resistance depth profiling (SRP). These techniques are capable of providing detailed USJ profile information, but at the expense of a turnaround time that is usually measured in days or even weeks or at the expense of damaging the surface with contacts.

Alternately, U.S. Publication No. 2004/0251927, assigned to the same assignee and incorporated here by reference describes a non-destructive MOR-type system for simultaneous measurements of junction depth (Xj) and abruptness. Systems of this type perform a series of measurements at different separations between the pump and probe beams followed by the analysis of measured data in I-Q space. A similar approach to measuring USJ depth and abruptness is described in the following publications: L. Nicolaides et al., Rev. Sci. Instrum. 74(1), 586 (2003) and A. Salnik et al., Rev. Sci. Instrum. 75(6), 2144 (2004) incorporated here by reference.

While USJ depth and abruptness are very important characteristics of the junction, they are not the only ones that the modern semiconductor manufacturing needs to control during the process. Other important parameters that define the quality of a junction are sheet resistance (Rs) and junction leakage current density ($I_0$).

In the prior art systems, Rs and $I_0$ have been measured using contact methods, such as four-point probe systems. These systems tend to damage the USJ layer that is becoming more and more shallow as the semiconductor technology pattern shrinks to 45 nm and beyond. Another example of non-contact technique that can characterize USJ electronic parameters is a Surface Photovoltage (SPV) technique. However, this method is only suitable for characterization of dynamic electronic properties of a USJ, such as carrier lifetime, carrier diffusion length, etc. In addition, SPV technology cannot produce the desirable accuracy and precision required for USJ manufacturing needs.

One of the recently introduced technologies that is capable of measuring both Rs and $I_0$ is so the called junction photovoltage (JPV) method that is similar in some aspects to SPV but eliminates certain disadvantages of the latter technology. An example of a production system using JPV technology is FSM RsL 100 Sheet Resistance and Leakage Current Mapping Tool from Frontier Semiconductor (San Jose, Calif.). In this system, the junction sheet resistance Rs and a junction leakage current $I_0$ are measured independently using the frequency dependencies of the JPV signal.

FIG. 1, is a schematic diagram illustrating one type of JPV tool which is discussed in more detail below. Further information about this type of tool can be found in "Non-contact electrical measurements of sheet resistance and leakage current density for ultra-shallow (and other) junctions," M. Faifer et al. MRS Symp. Proc. Vol. 810, pp. 475-480, April 2004; and "Non-contact sheet resistance and leakage current mapping for ultra-shallow junctions," M. Faifer, et al., Journal of Vacuum Science & Technology B: Microelectronics and Nanometer Structures, January 2006, Volume 24, Issue 1, pp. 414-420, both of which are incorporated herein by reference.

It would be desirable to have a single system capable of measuring all USJ parameters: junction depth, abruptness, carrier concentration, sheet resistance and leakage current density. Such a system would benefit semiconductor manufacturers as being able to perform a complete USJ characterization cheaper and faster.

SUMMARY OF THE INVENTION

The present invention provides a method for improved characterization of semiconductor samples and in particular ultra shallow junction measurements using a single tool that combines the MOR-type system capable of measuring junction depth, abruptness, carrier concentration and the JPV-type system suitable for measuring USJ sheet resistance and leakage current density.

In a preferred embodiment, the tool would include the basic elements of a modulated optical reflectometry measurement device. More specifically, the tool would include a light source for generating an intensity modulated pump beam. The pump beam is focused onto the sample in a manner to periodically excite a region of the sample to create an electron hole plasma. A second light source is provided for generating a probe beam which is directed to the sample within the periodically excited region. A photodetector monitors the modulated changes in the reflected probe beam induced by the periodic excitation and generating first output signals in response thereto.

In accordance with the subject invention, the tool is also configured to measure the effects of the periodic excitation on the electrical characteristics of the sample. Accordingly, the tool is further provided with a pair of capacitive electrodes positioned near the periodically excited region. A circuit is provided for measuring the modulated changes in the voltage at the electrodes induced by the periodic excitation and generating second output signals in response thereto. Finally, a processor is provided for analyzing the sample based on a combination of the first and second output signals.

Further objects and advantages of the subject invention will become apparent with reference to the detailed description taken in conjunction with the drawings in which:

DETAILED DESCRIPTION OF THE PREFERRED EMBODIMENT

Figure 1:
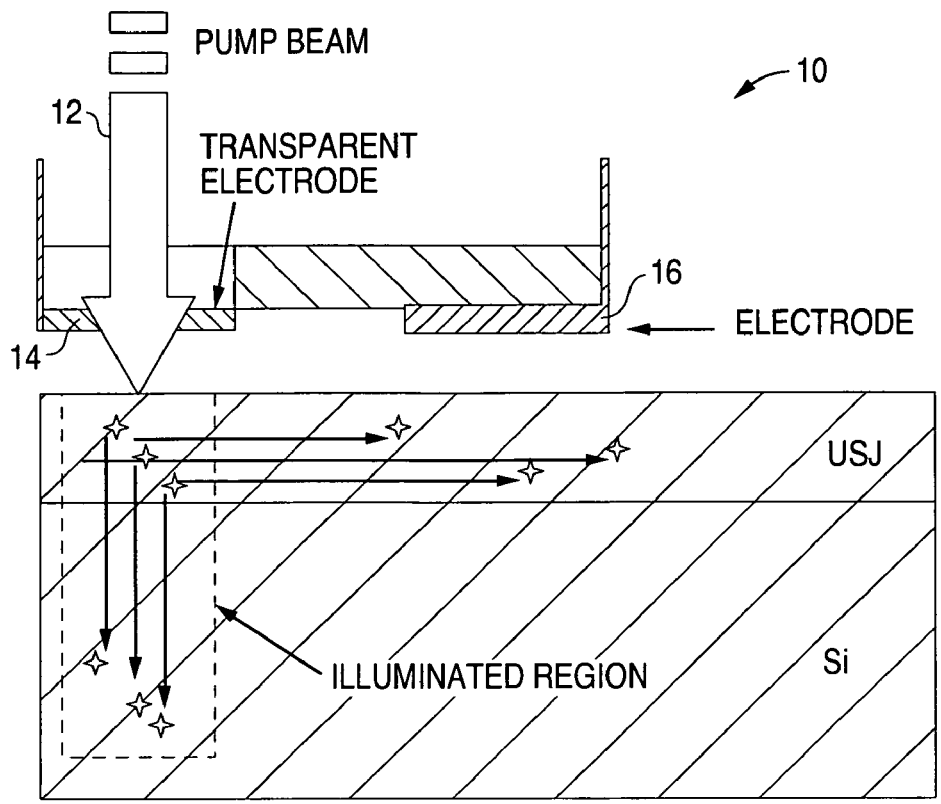
FIG. 1 is a schematic diagram of JPV type system found in the prior art.

The JPV-type system uses a non-contact method for determination of sheet resistance and leakage current density that combines photo-generation of carriers with the analysis of amplitude and phase of JPV signal. As depicted in FIG. 1, the JPV-type probe system 10 consists of an intensity modulated light beam 12 and two capacitive electrodes 14 and 16. Electron-hole pairs are created by the absorbed photon energy in the illumination region. The carrier diffusion and drift is monitored at the transparent 14 and offset 16 electrodes. The voltage under a probe follows a determined physical equation from which the sheet resistance Rs can be easily obtained. By analysis of the amplitude and relative phases of the JPV-type system as a function of light modulation frequency, the junction leakage current density $I_0$ may be determined in addition to Rs.

Similar to MOR technology, the physical principle of JPV is based on the absorption of light by the semiconductor sample and creation of electron-hole pairs which, in the case of USJ present in the sample, separate on the opposite sides of the junction forming a depletion layer. Created non-equilibrium carriers spread out from the generation site. Depending on the modulation frequency, this process is either plasma wave-like or diffusion driven and is affected by the junction sheet resistance Rs. Diffusion of charged carrier creates a voltage drop between the two electrodes that can be measured as a function of excitation light modulation frequency to determine the USJ leakage current $I_0$. At the limit of high modulation frequencies—on the order of 100 kHz for the most typical junctions—the JPV signal is determined almost solely by the junction sheet resistance Rs. In a simplified model, the junction sheet resistance Rs is related to the junction depth Xj through the electrical resistivity ρ of the junction material (silicon) as Rs=ρ/Xj. Therefore, the USJ depth Xj can be determined from the measured values of junction sheet resistance Rs.

JPV leakage current depends on both doping level and a residual damage left near the junction after the ion implantation and annealing manufacturing steps. Increasing the sub-junction damage increases the number of carrier recombination sites, thus increasing the leakage current. Therefore, the JPV measurements of junction leakage current provide important information about the quality of the junction and the presence of a residual damage at the junction edge.

Figure 2:
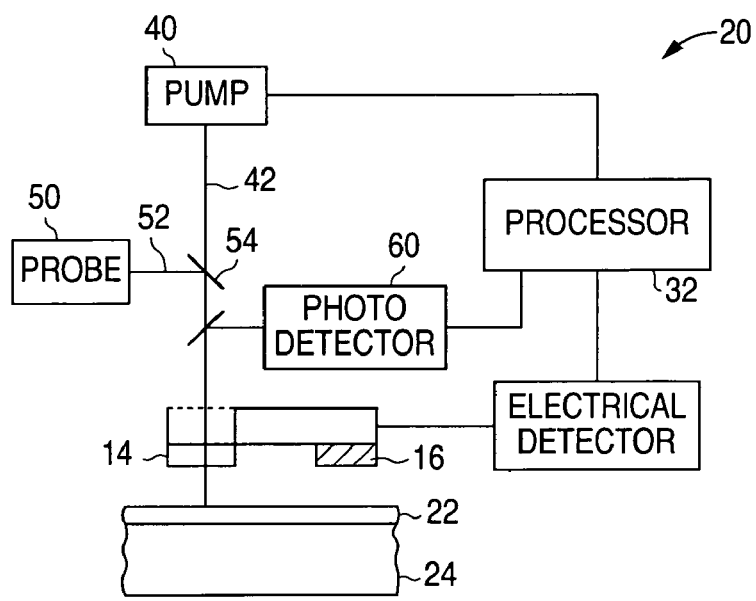
FIG. 2 is a schematic diagram of a combination system formed in accordance with the subject invention.

As discussed above, the MOR-type system uses an intensity modulated pump and non-modulated probe beams to characterize USJ properties. The presence of the transparent electrode in the JPV-type system and the requirement to have intensity modulated light beam (exiting the USJ sample through that window) simplifies the integration of the MOR- and JPV-type systems into a single device. FIG. 2 illustrates how the MOR system can be combined with the JPV system. Physically, this combination only requires the addition of the probe beam impinging on the sample through the same transparent electrode. Technically, the JPV system can be added to the assignee's existing Therma-Probe tool utilizing the MOR technology.

The system 20 of FIG. 2 is used to measure a sample wafer 22 located on a wafer support or chuck 24. The capacitive electrodes 14 and 16 of a JPV system are located above the wafer. (The size and spacing of the electrodes are exaggerated for the purposes of illustration). The output of the electrodes are connected to an electrical detector 30 which monitors the changing voltage between the electrodes. The output from the detector is supplied to a processor 32.

As noted above, in a JPV system, a light source 40 generates an intensity modulated pump beam 42. The modulation frequency of the pump beam is monitored and/or controlled by the processor. The processor monitors the modulated changes in the electrical signal generated by detector 30 that are synchronous with the pump beam modulation frequency. One skilled in the art will understand that various lock-in detection schemes can be used to monitor the amplitude and phase of the JPV measurements.

In accordance with the subject invention, a second light source 50 generates a probe beam 52. The probe beam is combined with the pump beam (typically by a dichroic mirror 54) and directed to the sample. In a preferred embodiment, the two beams are focused collinearly onto the sample with a microscope objective lens (not shown).

The reflected probe beam is directed to a photodetector 60. In a preferred embodiment, a filter (not shown) is provided to block pump beam light from reaching the detector. The photodetector monitors changes in the power of the beam and generates output signals in response thereto. These signals are supplied to the processor 32. Using lock-in detection techniques, the processor can derive the modulated changes in the reflected optical power signal that are synchronous with the pump beam modulation frequency (quadrature and in-phase signals). The processor can combine the signals from both detection systems in order to characterize the sample.

It should be noted that for any given sample, the optimum modulation frequency of the probe beam may not be the same for both the MOR and JPV measurements. Accordingly, it may be desirable to use one pump beam modulation frequency for the MOR measurement and a different pump beam modulation frequency for JPV measurement.

The combined system will benefit from a number of added features. For example, both MOR and JPV may be used for independent measurements of USJ depth Xj in the manner described above allowing for more accurate results. In this case, the MOR junction depth measurements may not require calibration to other independent technologies, i.e., SIMS.

In addition, the measured Rs in JPV technology may be used to characterize ion activation in a junction. These results may be compared to and analyzed together with the MOR measurements of the peak carrier concentration as described in the U.S. Publication No. 2006/0166385 assigned to the assignee of the present invention and incorporated herein by reference. (See also U.S. Patent Publication No. 2005/0195399, incorporated herein by reference.)

Still further, JPV's junction leakage current data may be used to characterize end-of-range residual damage and associated defects in a junction. These results may be compared to the damage relaxation curves obtained using the MOR system on the same sample.

Therefore, the combined system of the present invention will have extended USJ characterization abilities. Other benefits of combining the MOR and JPV technologies may be found by someone skilled in the art.

The results of the characterization of the wafer can be stored for later analysis. The results can be displayed in numeric form. Measurements taken over the surface of the wafer can be used to generate and display two dimensional wafer maps showing variations over the surface. The results of the measurements can also be used in feedback and feed forward techniques to vary, adjust or correct the semiconductor processing steps.

It should be noted that the method of present invention could be used not only for determination of USJ parameters discussed above. Also, given that some of the measurement parameters in both methods may be the same, a powerful combined tool can also be used for absolute measurements that do not require calibration to a standard sample. Applications of the combined system may also include post-implant and before-anneal wafers, SOI wafers, pre-amorphized wafers, and other samples.

It should also be noted that this combined system is useful both as described, and as a part of a more complex analytical instrument. More specifically, there may be cases where this system will be used in combination with related technologies, for example with the spectroscopic and/or photothermal radiometry techniques (See, U.S. Pat. No. 6,917,039, incorporated herein by reference).

Those skilled in the art will appreciate that the are a number of variants which are possible to the basic concept described herein. For example, in some cases it may be possible to monitor periodic changes in the displacement of the surface of the sample. In this case, the probe beam is typically displaced from the pump beam. Periodic angular deviations of the probe beam are monitored using a split cell detector. See U.S. Pat. Nos. 4,521,118 and 4,522,510, incorporated herein by reference.

Another variant uses an optical heterodyne approach to reduce the frequency of detection using. Such an optical approach is disclosed in U.S. Pat. No. 5,408,327, incorporated herein by reference. In the latter system, both the pump and probe beams are modulated but at slightly different frequencies. Both beams generate plasma effects at their respective modulation frequencies. The probe beam picks up an intensity modulation upon reflection due to the modulated optical reflectivity induced in the sample by the pump beam.

The MOR signal picked up upon reflection "mixes" with the inherent modulation of the probe beam, creating additional modulations in the probe beam at both the sum and difference frequency. This process is analogous to electrical heterodyning. The difference or "beat" frequency is much lower than either of the initial beam modulation frequencies and can therefore be detected by a low frequency lock-in amplifier.

While the subject invention has been described with reference to a preferred embodiment, various changes and modifications could be made therein, by one skilled in the art, without varying from the scope and spirit of the subject invention as defined by the appended claims.

We claim:

1. An apparatus for evaluating a semiconductor sample comprising:
    a light source for generating an intensity modulated pump beam;
    optics for directing the pump beam onto the sample in a manner to periodically excite a region of the sample and create an electron hole plasma;
    a light source for generating a probe beam which is directed to the sample within the periodically excited region;
    a photodetector for monitoring modulated changes in the reflected probe beam induced by the periodic excitation and generating first output signals in response thereto;
    a pair of capacitive electrodes positioned close to and spaced from the sample surface and near the periodically excited region;
    a circuit connected to said electrodes for measuring modulated changes in voltage induced by the periodic excitation and generating second output signals in response thereto; and
    a processor for analyzing the sample based on a combination of the first and second output signals.

2. An apparatus as recited in claim 1, wherein said photodetector measures changes in the modulated power of the probe induced by changes in optical reflectivity of the sample in response to the periodic excitation.

3. An apparatus as recited in claim 1, wherein one of said electrodes is transparent and said pump and probe beams are directed through said transparent electrode to the sample.

4. An apparatus as recited in claim 3, wherein said optics function to focus the pump and probe beams collinearly on the sample.

5. An apparatus as recited in claim 1, wherein said processor evaluates the characteristics of an ultrashallow junction based on the first and second output signals.

6. A method apparatus for evaluating a semiconductor sample comprising the steps of:
    directing an intensity modulated pump beam to the surface of the sample in a manner to periodically excite a region of the sample and create an electron hole plasma;
    monitoring the modulated changes of a reflected probe beam induced by the periodic excitation and generating first output signals in response thereto;
    positioning a pair of electrodes close to and spaced from the surface of the sample in the periodically excited region;
    monitoring the electrodes to measure modulated changes in voltage being induced by the periodic excitation and generating second output signals in response thereto;
    analyzing the sample based on a combination of the first and second output signals; and
    storing the results of the analysis.

7. A method as recited in claim 6, wherein the step of measuring the modulated changes of the probe beam is performed by measuring the modulated changes in the power of the probe beam induced by changes in optical reflectivity of the sample in response to the periodic excitation.

8. A method as recited in claim 6, wherein one of said electrodes is transparent and said pump and probe beams are directed through said transparent electrode to the sample.

9. A method as recited in claim 8, further including the step of focusing the pump and probe beams collinearly on the sample.

10. A method as recited in claim 6, wherein the characteristics of an ultrashallow junction are evaluated based on the first and second output signals.

* * * * *